(12) United States Patent
Rottenberg

(10) Patent No.: US 12,636,509 B1
(45) Date of Patent: May 26, 2026

(54) PHARMACOLOGICAL WEARABLE CARDIOVERTER DEFIBRILLATOR (WCD)

(71) Applicant: Eric Marc Rottenberg, Columbus, OH (US)

(72) Inventor: Eric Marc Rottenberg, Columbus, OH (US)

( * ) Notice: Subject to any disclaimer, the term of this patent is extended or adjusted under 35 U.S.C. 154(b) by 0 days.

(21) Appl. No.: 19/224,474

(22) Filed: May 30, 2025

(51) Int. Cl.
| | |
|---|---|
| *A61N 1/39* | (2006.01) |
| *A61M 5/142* | (2006.01) |
| *A61M 25/10* | (2013.01) |
| *A61N 1/04* | (2006.01) |
| *A61N 1/37* | (2006.01) |
| *G16H 40/63* | (2018.01) |

(52) U.S. Cl.
CPC ....... *A61N 1/3904* (2017.08); *A61M 5/14276* (2013.01); *A61M 25/1018* (2013.01); *A61N 1/046* (2013.01); *A61N 1/0484* (2013.01); *A61N 1/3702* (2013.01); *A61N 1/3925* (2013.01); *A61N 1/3987* (2013.01); *G16H 40/63* (2018.01); *A61M 2202/0007* (2013.01); *A61M 2202/04* (2013.01); *A61M 2205/04* (2013.01); *A61M 2205/054* (2013.01); *A61M 2210/125* (2013.01); *A61M 2230/04* (2013.01)

(58) Field of Classification Search
CPC .... A61N 1/3904; A61N 1/046; A61N 1/0484; A61N 1/3702; A61N 1/3925; A61N 1/3987; A61M 5/14276; A61M 25/1018; A61M 2202/0007; A61M 2202/04; A61M 2205/04; A61M 2205/054; A61M 2210/125; A61M 2230/04; G16H 40/63
See application file for complete search history.

(56) References Cited

U.S. PATENT DOCUMENTS

| | | | |
|---|---|---|---|
| 5,044,366 | A | 9/1991 | Alt |
| 5,228,438 | A | 7/1993 | Buchanan |
| 8,532,763 | B2 | 9/2013 | De Vos |
| 8,777,874 | B2 | 7/2014 | Zhang et al. |
| 11,793,423 | B2 | 10/2023 | Gunderson et al. |

(Continued)

OTHER PUBLICATIONS

Cammilli L, Mugelli A, Grassi G, Alcidi L, Melissano G, Menegazzo G, Silvestri V. Implantable pharmacological defibrillator (AlPhD): preliminary investigations in animals. Pacing Clin Electrophysiol. Feb. 1991;14(2 Pt 2):381-6. doi:10.1111/j.1540-8159.199.

*Primary Examiner* — Rex R Holmes

(57) ABSTRACT

The present invention provides a pharmacological wearable cardioverter defibrillation system for conducting cough assisted pharmacological cardioverter defibrillation during onset of a sudden arrhythmia. The system comprises a WCD defibrillator worn by the patient, a drug mix contained either in a reservoir/pump or in an inhaler, and a miniature monitor. The drug mix in the reservoir/pump is equipped with a pump for pumping the drug mix via an indwelling catheter to the coronary sinus while the drug mix in the inhaler is inhaled directly to the lungs. When a sudden arrhythmia is detected by a sensing electrode of WCD, the following steps are carried out: prompting the patient to take the drug mix, prompting the patient to start forceful coughing, and delivering electric shock(s) under either one of the two circumstances that the patient is unable to start coughing or the arrhythmia is not terminated.

4 Claims, 4 Drawing Sheets

(56)        References Cited

U.S. PATENT DOCUMENTS

2004/0172010 A1 *   9/2004   Addington .......... A61M 15/009
                                                          604/890.1
2016/0045754 A1     2/2016   Libbus et al.
2021/0369139 A1    12/2021   Muessig et al.
2023/0090464 A1 *   3/2023   Chapman ............... A61B 5/361
                                                          607/3

* cited by examiner

300

PHARMACOLOGICAL WEARABLE CARDIOVERTER DEFIBRILLATOR (WCD)

FIELD OF THE INVENTION

The present invention relates generally to a pharmacological cardioverter defibrillation system for improving efficacy of pharmacological cardioverter defibrillation and a method thereof. More specifically, the present invention relates to a cough assisted pharmacological cardioverter defibrillation system.

BACKGROUND

Ventricular tachycardia (VT) and ventricular fibrillation (VF) are important causes of mortality and morbidity in a wide variety of heart diseases. Although the use of implantable cardioverter defibrillators (ICDs) or pacemakers are commonplace in patients with chronic heart arrhythmia or chronic heart failure, ICD is replaced by a wearable cardioverter defibrillator (WCD) for patients who are not candidates for an implantable defibrillator.

A WCD comprises a monitor worn at the waist and a vest-like garment. The garment includes multiple sensing electrodes and shocking electrodes. The electrodes serve as defibrillation pads. Electrocardiogram (ECG) signals of WCDs are recorded from two pairs of sensing electrodes placed circumferentially at the level of the xiphoid process. The signals are continuously processed by a WCD proprietary algorithm that digitally filters and analyzes the ECG from each electrode pair.

Although WCDs provide protection against increased risk of sudden cardiac death, WCDs may be impacted by inappropriate shocks (IAS). IAS is caused by tachycardias, motion artifacts, and oversensing of low-level electrical signals. The tachycardias includes atrial fibrillation (AF), supraventricular tachycardia (SVT), and non-sustained ventricular tachycardia/fibrillation (NSVT/VF). Physical activities responsible for motion-induced IAS include riding a motorcycle, lawnmower, or tractor. These shocks may be arrhythmogenic, result in injuries, precipitate WCD discontinuation, and consume medical resources. In some cases, they also can be lethal.

Furthermore, WCDs are prone to interference from a variety of external sources, one of which is bystander cardiopulmonary resuscitation (CPR). This happened to a patient with cardiac arrest 3 months after a large inferior wall myocardial infarction (MI), who was wearing a WCD at the onset of his cardiac arrest. Because his co-workers gave him CPR within 30-60 seconds before the WCD could detect VF and deliver the warning, bystander CPR was responsible for hindering the detection algorithm, which ultimately canceled the appropriate rescue shock.

SUMMARY OF THE PRESENT INVENTION

The present invention provides a cough-assisted pharmacological cardioverter defibrillation system and a method of using the system. According to one of the embodiments, the method consists of replacing the electric shock with retroperfusing a drug mix into the coronary sinus immediately after a sudden heart arrhythmia arises. According to another one of the embodiments, the method consists of replacing the electric shock with taking a drug mix in the form of aerosol through the mouth to the lungs immediately after a sudden heart arrhythmia arises. The circulation of the drug mix to the heart muscles is assisted by forceful coughs self-administered by the patient. The self-administered forceful cough by the patient is also called cough cardiopulmonary resuscitation (cough CPR).

A WCD is incorporated in the defibrillation system of the present invention. The WCD is used for continuously monitoring the patient's heart rhythm, sending an alert to the patient at the onset of a sudden arrhythmia, and delivering electric shocks under circumstances that either the patient is unable to respond, or the arrhythmia is not terminated.

In the cases in which the WCDs are known to deliver IAS, a miniature monitor is added to interface with the WCD. The miniature monitor, which comprises two sensing electrodes, is used to monitor the patient's heart rhythm and send an alert to the patient at onset of a sudden arrhythmia, thereby requesting the defibrillation unit of the WCD to deliver electric shocks.

The objective of the present invention is to provide an improved pharmacological cardioverter defibrillation system and method thereof. The system and the method are for the purpose of increasing the efficacy of defibrillation and avoiding unnecessary painful electric shock(s) for patients during onset of a sudden heart arrhythmia.

According to one of the embodiments of the present invention, the apparatus for the defibrillation includes a WCD worn by the patient and a drug container filled with a drug mix. The drug container may be a reservoir/pump filled with a drug mix, of which the pump is attached to the reservoir for pumping the drug mix to coronary sinus of the patient. The reservoir/pump is connected to an indwelling catheter with one end placed in the coronary sinus of the patient and the other end in the drug reservoir/pump. The drug container may also be a handheld inhaler. The WCD includes electrodes attached to the patient's chest wall and a WCD monitor. The electrodes include sensing electrodes to monitor the heart rhythm and shocking electrodes for delivering electric shocks. The WCD monitor includes an electrocardiogram (ECG) unit and a defibrillation unit. The WCD monitor sends an alert to the patient when a sudden arrhythmia arises.

According to another one of the embodiments of the present invention, the apparatus for the defibrillation include a WCD worn by the patient, a drug container filled with a drug mx, and a miniature monitor configured to interface with the WCD. The drug container may be a reservoir/pump filled with a drug mix, of which the pump is attached to the reservoir for pumping the drug mix to coronary sinus of the patient. The reservoir/pump is connected to an indwelling catheter with one end placed in the coronary sinus of the patient and the other end in the drug reservoir/pump. The drug container may also be a handheld inhaler. The WCD includes shocking electrodes attached to the patient's chest wall for delivering electric shocks and a monitor. The WCD monitor includes a defibrillation unit. The miniature monitor sends an alert to the patient when the sensing electrodes of the miniature monitor senses a sudden arrhythmia.

When a sudden arrhythmia is detected by the sensing electrodes, the defibrillation method of the present invention comprises the following steps: confirmation of a lethal arrhythmia (VF or VT) by the WCD monitor or the miniature monitor for the WCDs known to deliver IAS, prompting the patient to take the medicine of drug mix by either injection to the coronary sinus or inhalation to the lungs and simultaneously start forceful coughs. The cough should generate adequate cardiac output to perfuse not only the brain through the carotid arteries, but also the heart through the coronary artery. The forceful cough induced cardiac output would adequately circulate the drug mix to the heart muscles, thereby theoretically achieving drug-induced defibrillation. Under either one of the two circumstances that the patient is unable to start coughing (coughing creates significant electrocardiogram (ECG) artifacts; therefore, if no artifacts detected, the patient did not start coughing) or the VT or VF is not terminated, electric shock(s) will be delivered to the patient by the defibrillator unit of WCD. Before delivering the electric shock, a conductive gel is released to a patient's skin area between the defibrillation pads and the patient chest wall.

BRIEF DESCRIPTION OF THE DRAWINGS

The methods of cough assisted pharmacological cardioverter defibrillation are the disclosure herein of exemplary embodiments of the present invention. It is distinctly claimed in the claims at the conclusion of this patent description. The foregoing and other features and advantages of the present invention will become more apparent from the following detailed description taken in conjunction with the accompanying drawings.

DETAILED DESCRIPTIONS OF THE INVENTION

WCDs, like implantable defibrillators, provide therapeutic electric shocks to the hearts of patients at the onset of a sudden arrhythmia. The present invention incorporates the WCD defibrillators with a cough assisted pharmacological defibrillation procedure for the purpose of improving efficacy of defibrillation and avoiding unnecessary painful electric shocks to the patients.

Although the invention has been explained in relation to its preferred embodiments, it is to be understood that many other possible modifications and variations can be made without departing from the spirit and scope of the invention.

Reference will be made in detail to exemplary embodiments of the invention, which are illustrated in the accompanying drawings.

Figure 1:
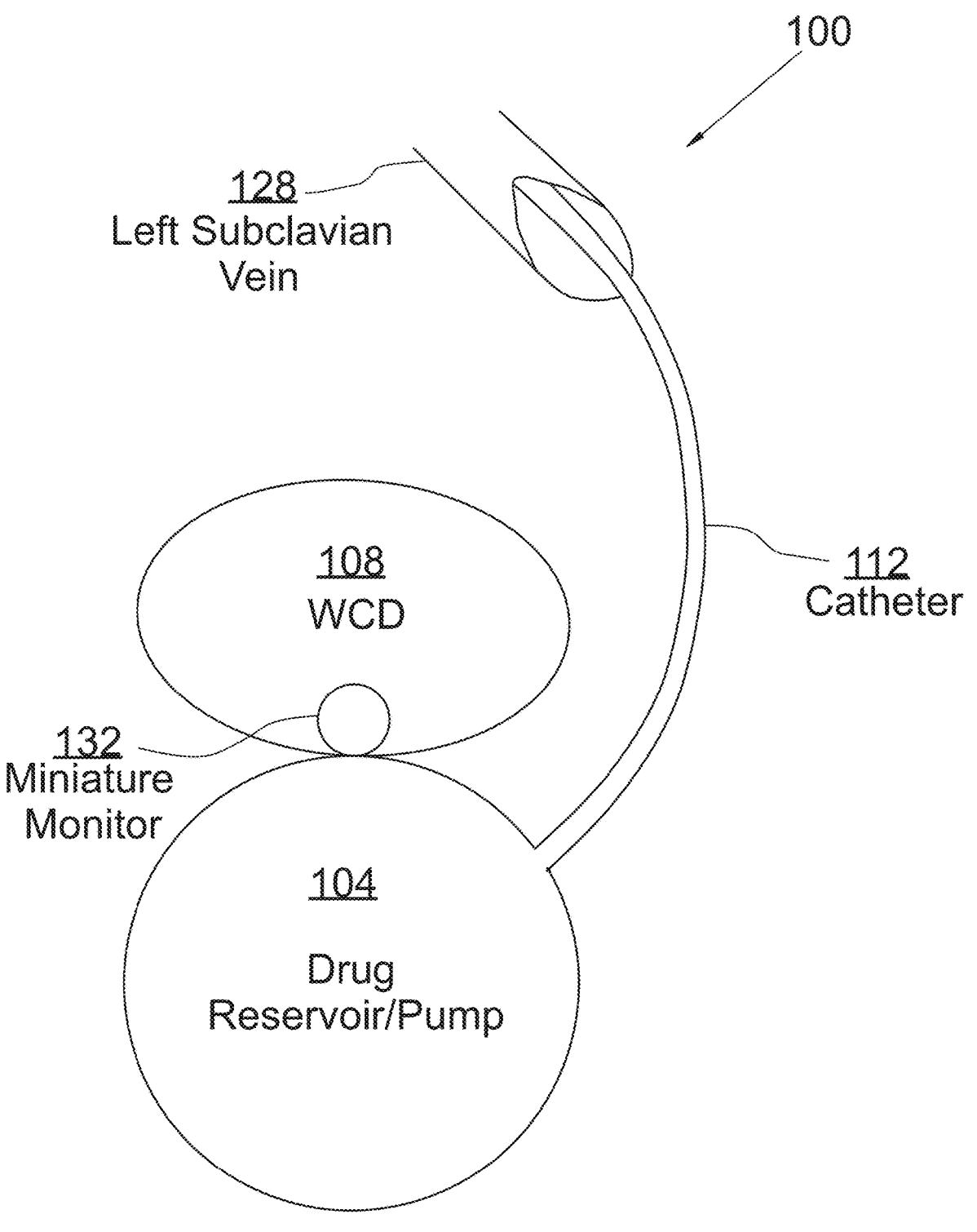
FIG. 1 is a schematic diagram illustrating pharmacological cardioverter defibrillation system according to one of the embodiments of the present invention.

Referring to FIG. 1, there illustrated is a schematic diagram 100 illustrating pharmacological cardioverter defibrillation system according to one of the embodiments. The apparatus includes a drug mix reservoir/pump 104, a WCD 108, an indwelling balloon-tipped coronary sinus catheter 112 with one end inserted in the coronary sinus and the other end in the drug mix reservoir/pump, and a miniature monitor 132. The WCD 108 comprises electrodes, including a first set of sensing electrodes and shocking electrodes. The first set of sensing electrodes are used for monitoring heart rhythm and recording electrocardiogram (ECG) data while the shocking electrodes are used for delivering electric shocks. The reservoir/pump 104 is placed under the patient's skin and filled with the drug mix, which can be externally refilled. The drug mix can be removed and replaced when necessary.

The WCD includes a WCD monitor in addition to the miniature monitor. The WCD monitor comprises an ECG unit and a defibrillation unit. The ECG unit is connected to the sensing electrodes on the patient's chest wall to monitor the heart rhythm. The ECG unit is interfaced with the defibrillator unit of WCD worn by the patient. A shock is delivered through the shocking electrodes (which also serve as defibrillation pads) at the request of the defibrillator unit when a lethal rhythm is detected.

Before a treatment sequence begins, the WCD identifies and validates the presence of a treatable arrhythmia. Once confirmed, an alarm sequence begins, and an audible prompt to the patient into the sequence. Blue conductive gel is released to the skin between the defibrillation pads and chest wall of the patient. Treatment occurs within one minute. Patients can prevent a shock during an alarm sequence at any time by pressing and holding the response buttons on the monitor. Releasing the response buttons causes the alarm sequence to restart provided the arrhythmia detection persists.

The miniature monitor 132 is connected via wires to a second set of two sensing electrodes on the chest. One sensing electrode is placed below the left clavicle (mid clavicular area) and the other below the right clavicle (mid clavicular area). The miniature monitor 132 is configured to interface with the WCD. The second set of sensing electrodes monitor the heart rhythm of patients and communicate with the defibrillation unit of WCD.

When the WCD's monitor is known to falsely detect a shockable rhythm, which would result in delivering IAS, the miniature monitor 132 and the second set of sensing electrodes will replace the WCD monitor and the first set of sensing electrodes for monitoring the patient's heart rhythm, thereby sending an alert to the patient at onset of a sudden arrhythmia and requesting the defibrillation unit of the WCD to deliver electric shocks under circumstances that either the patient is unable to start coughing or the arrhythmia is not terminated.

One of the monitors, which is either the miniature monitor or WCD monitor, is configured to interface with the drug reservoir/pump 104 according to some embodiments of the present invention. When the drug reservoir/pump is either empty or the drug mix needs to be replaced due to expiration of one or more compositions, the reservoir/pump will send a signal to the monitor to request a refill.

Either the ECG unit of WCD or the miniature monitor sends an alert to the patient when a sudden heart arrhythmia arises. If the VF or VT is not terminated, a signal is sent to the defibrillator unit, requesting shocking electrodes to deliver a shock. Because the effect of the drug mix on the arrhythmia of a particular patient is unknown, an electric shock will be given if VT is not terminated. However, it is emphasized that the ECG unit of WCD must not be able to trigger an electrical shock or prompt delivery of the drug mix when VF or VT is initially detected unless it is confirmed by the miniature monitor in WCDs known to deliver IAS.

As shown in FIG. 1, the indwelling catheter 112 is inserted via the left subclavian vein 128 and then fluoroscopically guided into the coronary sinus. The catheter 112 transports the drug mix from the reservoir 104 to the coronary sinus 204 according to one of the embodiments of the present invention. Once the catheter 112 is placed, it permanently stays in place. Placement of the catheter tip is 1 to 2 cm proximal to the left atrial appendage, which allows liberal infusion without wedging of the tip. Once placed, it is connected to the reservoir/pump 104. There are a few points to pay attention to when inserting the catheter: (1) insert the catheter high in the right atrium via the subclavian vein, close to the right atrial appendage; and (2) do not bend the catheter.

Figure 2:
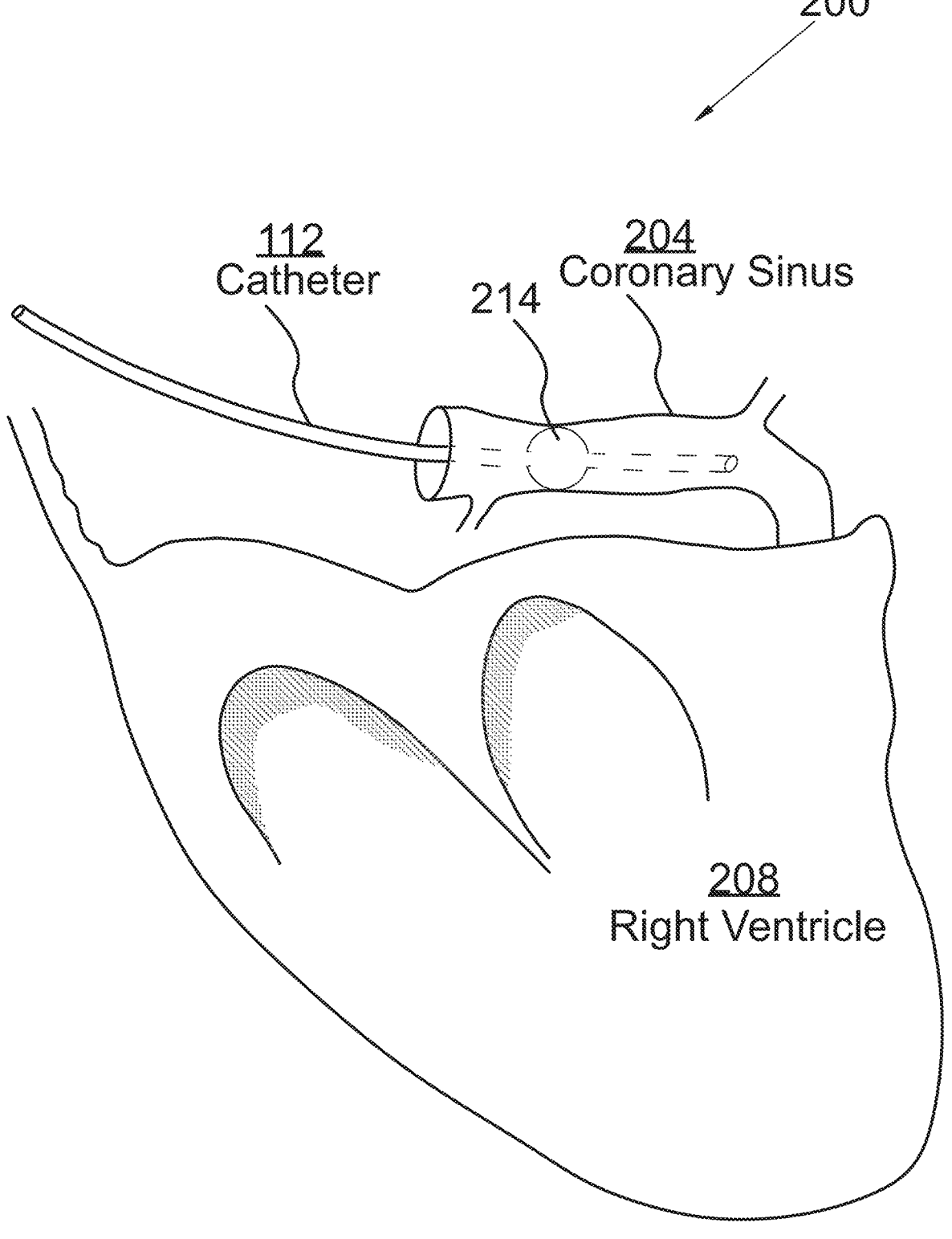
FIG. 2 is a schematic view of the catheter with a balloon inserted in the coronary sinus according to another one of the embodiments of the present invention.

Referring to FIG. 2, there illustrated is a schematic view 200 of the catheter 112 with an inflatable balloon 114 inserted in the coronary sinus 204 according to one of the embodiments of the present invention. Confirmation of the catheter placement is obtained by manually palpating the catheter 112 or the inflated balloon 114 in the atrioventricular groove. If not felt, it is certain that the catheter is not in place and most likely is in either the right ventricle or inferior vena cava. The catheter 112 may be secured by snaring the catheter and ligating with a free tie around the movable ring on the cannula, after checking to assure there is no excessive catheter loop in the right atrium.

A major function of the balloon 114 is to temporarily occlude the coronary sinus 204 for infusing contrast media, drugs, or therapeutic agents, or for possible introduction of devices into the coronary venous system. Thus, the balloon 114 of the coronary sinus catheter is inflated to close the coronary sinus before injecting the drug mix. The pump of the drug reservoir/pump 104 has a built-in wireless mechanism so that it can receive signals from either the ECG unit of WCD or the miniature monitor to inflate the balloon before injecting the drug mix into the coronary sinus once VF or VT is detected.

Once the arrhythmia is terminated, a signal is sent from the monitor to the pump to deflate the balloon. However, in practice, the patient must be accounted for to decide when to deflate the balloon. Also, in the cases that the arrhythmia is not terminated by pharmacological defibrillation, the balloon needs to be deflated before delivering the electric shock(s).

The balloon may have another function in assisting the catheter insertion into the coronary sinus. Although the catheter insertion is successful in most cases, there are occasional cases when advancement of the catheter into the greater cardiac vein is not possible due to anatomical variations. In these situations, the balloon is moderately inflated, and the drug mix infusion is begun while the surgeon's right index or long finger is pressed distal to the balloon to prevent dislodgement.

According to an embodiment of the invention, the balloon inflation procedure may be replaced by a self-administered cough CPR. Cough CPR is initiated by one of the monitors to send a signal through a controlling audio/voice to prompt the patient to self-administer forceful cough CPR after the drug mix is injected. On the other hand, the cough CPR could greatly assist blood flow within the heart with the balloon inflated, reducing the time needed for the balloon to be deflated.

A cough is produced by closing the glottis, followed by a strong contraction of the respiratory muscles (diaphragm and intercostal muscles), which rapidly increases the intrathoracic pressure, resulting in the explosive discharge of airway contents when the glottis is re-opened. Thus, a forceful cough may yield high intrathoracic pressure and high intraabdominal pressure, which improves perfusion during the arrhythmia. Since the heart is within the thoracic cavity, the heart is subjected to the same rapid rise in pressure as the lungs. It is postulated that this compressive force propels blood forward because of the presence of valves in the heart.

In a case study of 8 patients in the laboratory, the study demonstrated that after VF was detected, forceful coughing was prompted every 1-3 seconds in which the patients maintained consciousness for 24-39 seconds. Essentially cough-induced cardiac compression was achieved.

Cough CPR is patient self-administered according to some embodiments of the present invention. The coughing assistance during the pharmacological defibrillation provides the following advantages: 1. produces an arterial pressure pulse; 2. produces opening of the aortic valve; 3. generates forward blood flow; and 4. maintains consciousness during circulatory arrest. Consequently, coughing could generate adequate cardiac output to perfuse not only the brain through the carotid arteries, but also the heart through the coronary artery, which adequately circulates the drug mix to the heart muscles, thereby theoretically achieving drug-induced defibrillation.

Pharmacological defibrillation in the presence of a WCD is carried out by injecting a drug mix into the coronary sinus soon after a sudden heart arrhythmia has occurred. The drug mix is retro perfused into the coronary bed through the coronary sinus, replacing the electric shock with a chemical one. Hearts are defibrillated by infusing the drug mix, which effectively slows and synchronizes electrical activity.

Figure 3:
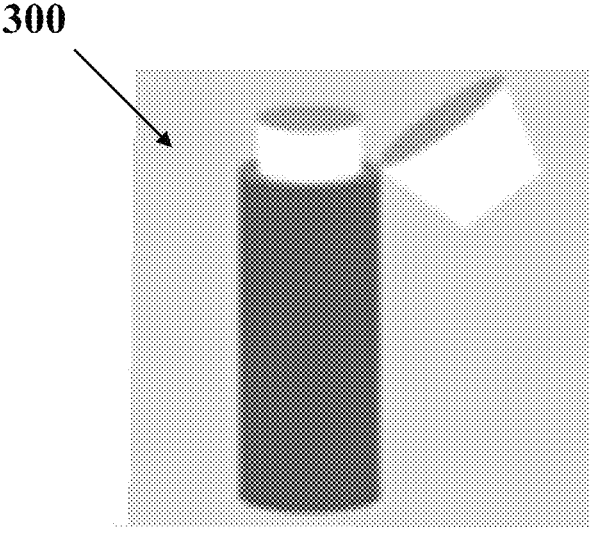
FIG. 3 is a schematic view of an inhaler filled with the drug mix in the form of soft mist according to one of the embodiments of the present invention.

Referring to FIG. 3, there illustrated is a schematic view of an inhaler 400. According to another embodiment of the present invention, the drug mix may be sprayed into the patient's mouth using the inhaler at the onset of VF or VT. The inhaled drug mix gets directly to the lungs. Simultaneously, the patient is prompted to start cough CPR. This approach replaces injection of the drug mix through the catheter to the coronary sinus.

The inhaler 300 is a small, handheld device that delivers medication directly to a patient's lungs. The drug mix in the inhaler can be metered-dose, dry powder, or soft mist. A common drug form of the soft mist is the aerosol liquid, which comprises fine solid particles or liquid droplets suspended in air or another gas.

The drug mix may comprise components such as, but not limited to, dibenzepin and epinephrine or other chemicals in the same families. Dibenzepin was reported to increase VF threshold and to cause spontaneous termination of electrically induced VF in mammals. However, the dibenzepin used alone has limited efficacy. It was also reported that hearts were readily defibrillated by infusing a mixture of dibenzepin and epinephrine, which effectively slowed and synchronized electrical activity of the heart. In certain circumstances, injecting the mixture of dibenzepin and epinephrine into the coronary sinus is necessary for improving the effectiveness of the electric defibrillation and for preventing rearrest.

A feasibility study of drug-induced ventricular defibrillation was conducted on pigs. Five to ten days old male landacre pigs (total number: 16) were anaesthetized, ventilated, and subjected to sternotomy. According to an e-mail communication from the lead author (Dr. Thomas Podzuweit), the sternum was separated from the ribcage and put back in place such that downward displacement of the sternum allowed effective-depth direct cardiac massage without touching the heart. He also believed that the drug mix of dibenzepin and epinephrine would increase the effectiveness of electrical defibrillation. A balloon-ECG and aortic pressure were recorded. VF was induced by the brief electrical stimulation of ventricular epicardium. 15 to 75 seconds after the onset of VF, drugs or vehicle, which were infused and distributed by cardiac massage, are as follows: A. isotonic saline (vehicle), B. epinephrine (2.5 µg/kg), C. dibenzepin (7.5 mg/kg), D. a mix of dibenzepin and epinephrine (B+C). The drugs or vehicle was dissolved in saline.

In control experiments with infusion of vehicle, none of the animals survived. Similarly, the administration of dibenzepin or epinephrine alone did not cause defibrillation. However, hearts were readily defibrillated by infusing a mix of both dibenzepin and epinephrine compounds, which effectively slowed and synchronized electrical activity. When VF was induced again in the medicated pig, it was of short duration, easing within 2-3 minutes, thereby ultimately preventing rearrest. This study demonstrated consistent drug-induced defibrillation in young domestic pigs, indicating that VF is a potentially reversible condition and can be rectified by pharmacotherapy.

In addition to the drug mix of dibenzepin and epinephrine, other antidepressants, such as maprotiline, catecholamines, and cyclic adenosine monophosphate (cAMP), are composition candidates in the drug mix. They have an effect on VF and collateral blood supply following acute coronary occlusion. The above-mentioned compounds and hormones may convert VF to a transient VF that reverts spontaneously into a sinus rhythm. Furthermore, it is known that a high catecholamine level in the heart increases intercellular coupling, thereby improving conductivity and shortening conduction time.

Figure 4:
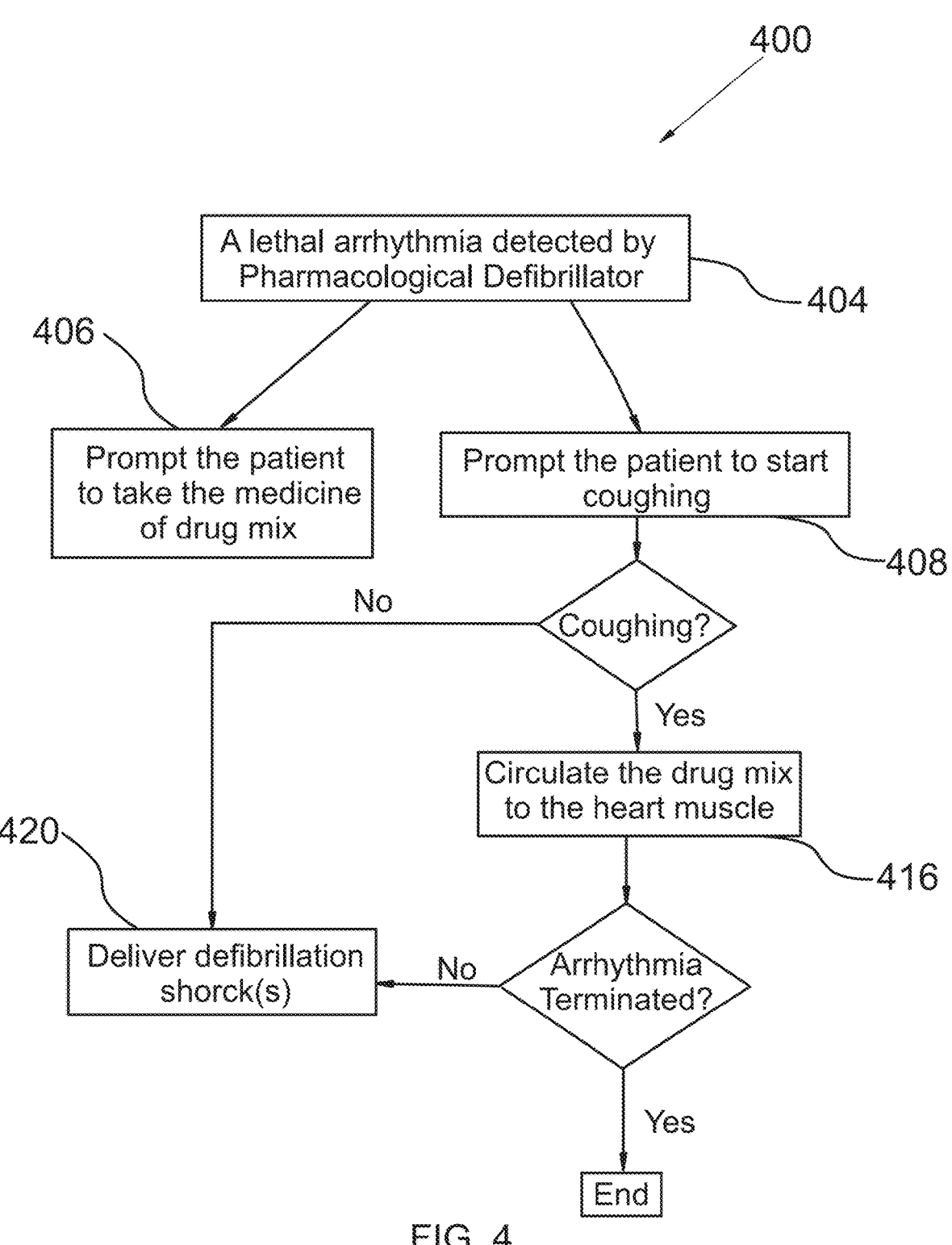
FIG. 4 is a flow diagram of the pharmacological cardioverter defibrillation according to one of the embodiments of the present invention.

Referring to FIG. 4, there illustrated is a flow diagram 400 of the cough-CPR assisted pharmacological defibrillation according to one of the embodiments of the present invention. According to the flow diagram, when a sudden heart arrhythmia is detected by a WCD 404, one or two of the monitors sends ECG data and mechanical alert to the patient and/or a medical doctor. At the request of the patient or the medical doctor, the drug mix is taken by the patient either by injection into the coronary sinus via the indwelling catheter or by inhalation into the lungs 406. In some embodiments, when the balloon of the catheter is involved in the defibrillation, the balloon is inflated before injecting the drug mix. The patient is immediately prompted to start forcefully coughing 408. The coughing may achieve drug-induced defibrillation 416. However, if it is detected that the patient does not start coughing, the defibrillation unit delivers electric shock(s) 420. Also, if the arrhythmia is not terminated, the defibrillation unit also delivers electric shock(s) 420. In the case that the drug reservoir/pump is used for injecting the drug mix, before delivering the electric shock(s), the balloon of the catheter is to be deflated. Also, before delivering the electric shock(s), a conductive gel is released to the skin area between the patient's chest wall and the defibrillation pads. One of the great values of the pharmacologic defibrillation is that a painful shock may be able to be avoided.

The present invention has been described in terms of exemplary embodiments for the purpose of illustration. People skilled in the art will recognize from this patent description that the invention is not limited to the embodiments described but may be practiced with modifications and alterations limited only by the spirit and scope of the appended claims. For example, new generations of defibrillating antiarrhythmic drugs will be postulated in the future.

What is claimed is:

1. A method of providing a pharmacological cardioverter defibrillation, the method comprising:

providing a wearable cardioverter defibrillation system (WCD) worn by a patient, the WCD including electrodes placed on the patient's chest wall, the electrodes including a first set of sensing electrodes and shocking electrodes, and a WCD monitor, the WCD monitor including an ECG unit and a defibrillation unit, wherein the sensing electrodes monitor the heart rhythm and communicate with the ECG unit, and the shocking electrodes communicate with the defibrillation unit and deliver electric shock(s) at request of the defibrillation unit;

providing a drug container filled with a drug mix; and wherein the drug mix comprises dibenzepin and epinephrine; and conducting following steps when a sudden heart arrhythmia is detected by the sensing electrode(s):

prompting or assisting the patient to take the drug mix;

prompting the patient to start forceful coughing; and delivering electric shock(s) by the defibrillation unit of WCD under either one of the two circumstances that the patient is unable to start coughing or the arrhythmia is not terminated.

2. The method of claim 1, wherein the drug container comprises a drug reservoir/pump, the pump attached to the reservoir for pumping the drug mix to coronary sinus of the patient via an indwelling catheter, the reservoir/pump placed under skin of the patient.

3. The method of claim 2, wherein the catheter further includes an inflatable balloon positioned inside the coronary sinus; and wherein the method further comprises a step of inflating the balloon to close the coronary sinus before pumping the drug mix and a step of deflating the balloon either before delivering the electric shocks or after the arrhythmia is terminated.

4. The method of claim 1, wherein the drug container comprises an inhaler.

* * * * *